United States Patent [19]

Schutz

[11] Patent Number: 5,055,620

[45] Date of Patent: Oct. 8, 1991

[54] PROCESS FOR ALDOL CONDENSATION

[75] Inventor: Alain A. Schutz, Plum Borough, Pa.

[73] Assignee: Aristech Chemical Corporation, Pittsburgh, Pa.

[21] Appl. No.: 576,909

[22] Filed: Sep. 4, 1990

Related U.S. Application Data

[62] Division of Ser. No. 339,745, Apr. 18, 1989, Pat. No. 4,970,191.

[51] Int. Cl.$^5$ .............................................. C07C 45/45
[52] U.S. Cl. .................................. 568/353; 568/388; 568/461
[58] Field of Search ...................... 568/353, 461, 388

[56] References Cited

U.S. PATENT DOCUMENTS

| | | | |
|---|---|---|---|
| 3,337,633 | 8/1967 | Schmitt et al. | 260/586 |
| 3,554,929 | 1/1971 | Aarons | 252/462 |
| 3,702,882 | 11/1972 | Rettew et al. | 423/600 |
| 3,946,079 | 3/1976 | Mizutani et al. | 260/593 R |
| 4,059,632 | 11/1977 | Cane et al. | 260/586 C |
| 4,086,188 | 4/1978 | Reichle | 252/473 |
| 4,165,339 | 8/1979 | Reichle | 260/586 C |
| 4,256,722 | 3/1981 | Carrier | 423/594 |
| 4,400,431 | 8/1983 | Henslee et al. | 428/402 |
| 4,458,026 | 7/1984 | Reichle | 502/80 |
| 4,471,070 | 9/1984 | Siefert et al. | 502/302 |
| 4,472,532 | 9/1984 | Mooi | 502/302 |
| 4,476,245 | 10/1984 | Siefert | 502/302 |
| 4,492,677 | 1/1985 | Yoo et al. | 423/244 |
| 4,492,678 | 1/1985 | Yoo et al. | 423/244 |
| 4,495,304 | 1/1985 | Yoo et al. | 502/66 |
| 4,495,305 | 1/1985 | Yoo et al. | 502/65 |
| 4,522,937 | 6/1985 | Yoo et al. | 502/302 |
| 4,535,187 | 8/1985 | Papa et al. | 568/353 |
| 4,656,156 | 4/1987 | Misra | 502/415 |
| 4,728,635 | 3/1988 | Bhattacharyya et al. | 502/304 |

OTHER PUBLICATIONS

G. S. Salvapati et al, "Selective Catalytic Self-Condensation of Acetone", Journal of Molecular Catalysis, 54 (1989), pp: 9-30.

*Primary Examiner*—James H. Reamer
*Attorney, Agent, or Firm*—William L. Krayer

[57] ABSTRACT

Basic mixed oxides useful for base catalyzed reactions such as the aldol condensation of acetone and also useful as catalyst supports are made by mixing an acid such as nitric acid or acetic acid with a pseudoboehmite to form a gel, adding magnesium oxide or hydroxide, in a ratio of magnesium to aluminum of about 1:1 to about 10:1, agitating and heating for about 1 to 24 hours, and subsequently drying and calcining. The resulting polymorphic magnesium-aluminum oxide composition is hightly effective in the aldol condensation of acetone to isophorone, and other base catalyzed reactions such as isomerization of olefins, aldol condensation of aldehydes.

10 Claims, 2 Drawing Sheets

PROCESS FOR ALDOL CONDENSATION

This is a division of application Ser. No. 339,745, filed Apr. 18, 1989 now U.S. Pat. No. 4,970,191.

TECHNICAL FIELD

This invention relates to new catalysts, methods of making them, and certain aldol condensations employing them. In particular, it relates to a method of making a catalyst or catalyst support whereby a pseudoboehmite is peptized with an acid to form a dispersion or gel, which is then reacted with magnesium oxide; the material is then dried and calcined. The catalyst may be used for making mesityl oxide and isophorone from acetone.

BACKGROUND ART

Prior to the present invention, it has been known to prepare catalysts and catalyst supports from pseudoboehmite, particularly by calcination of the pseudoboehmite to aluminum oxide or more specifically gamma alumina. Pseudoboehmite is a material of choice because of its reactivity, availability and forming properties. This material is widely used as a catalyst support and catalyst for many chemical processes.

However, a very particular property of pseudoboehmite derivatives is that they are mainly acidic which is usually useful for catalytic reactions which involve carbo-cation intermediates, such as in alcohol dehydration, skeletal isomerization, ring alkylation, and cracking of hydrocarbons. When they are used as supports, their acidity is usually necessary for activation of a catalytic agent such as nickel, platinum, or molybdenum in a bifunctional mechanism needed for the desired reaction.

Prior to the present invention, it has been known to convert acetone to isophorone and mesityl oxide by condensation in the presence of a catalyst made by reacting (or "interacting") certain aluminum salts with certain magnesium salts or hydroxides—see Reichle, U.S. Pat. Nos. 4,165,339 and 4,458,026. A catalyst described as "Mg-Al-$CO_3$ Hydrotalcite Catalyst" and similar compositions were proposed in the examples of Reichle's U.S. Pat. No. 4,458,026, using as ingredients such materials as $Mg(NO_3)_2.6H_2O$ and $Al_2(NO_3)_3.9H_2O$ together with sodium carbonate. Synthetic hydrotalcites (Joint Committee on Powder Diffraction Standards files #14-191 and 22-700) sometimes also referred to as a magnesium aluminum hydroxy carbonate are also proposed in U.S. Pat. Nos. 4,656,156 and 4,476,324. Other similar catalyst compositions containing magnesium and aluminum are disclosed in U.S. Pat. Nos. 4,539,195 and 4,086,188. Such compositions are not made from the mixed oxides of magnesium and aluminum, however, but generally begin with at least one salt or hydroxide, which affects the crystalline structure of the final composition. The method of "interacting" the salts has become known as the co-precipitation method.

Various mixed oxides are reviewed in Papa's U.S. Pat. No. 4,535,187, which contains the statement (col. 1, lines 48–51) "The co-precipitated mixed oxide catalysts have the drawback of exhibiting poor catalyst manufacturing reproducibility and are expensive." The review, however, does not include a discussion of a mixture of aluminum and magnesium oxides.

DISCLOSURE OF INVENTION

The present invention differs from the above described various methods of obtaining catalysts containing magnesium and aluminum in that it employs a particular sequence of steps not heretofore described and obtains a catalyst composition different from those described in the past.

In the present invention, pseudoboehmite is used as one of the main components for the preparation of the catalyst. It is reacted with magnesium oxide (or magnesium hydroxide) to form a mixed metal hydroxide which yields after calcination an oxide possessing strong basic properties. Such properties are used to catalyze reactions via carbanionic species. Typical base catalyzed reactions which can be conducted with my catalyst are double bond migration of olefins, side-chain alkylation of alkylaromatics, Michael reactions, Aldol condensations, alkylation of phenol at the ortho-positions, oxygen-sulfur-nitrogen interchange reactions, polymerization of lactones and decomposition of methyl formate.

In the examples and discussion below (and throughout this application) pseudoboehmite means small crystallites of Boehmite or AlOOH having an X-ray diffraction pattern corresponding to the JCPDS file #21-1307. Broad X-ray lines are characteristic of the crystallites size of this material. Pseudoboehmite has the property of being dispersed with acid into colloidal particles (positively charged particles having sizes less than one micron in diameter) but not of being soluble in dilute acid. This material is commercially available under the name of VERSAL, CATAPAL, PSEUDOBOEHMITE, or DISPERAL. I prefer to use acetic acid, but any water soluble organic or inorganic acid can be used.

More specifically, I have found that I may begin with a pseudoboehmite or an amorphous gel of aluminum hydroxide, mix it with, approximately, an equivalent of an inorganic or organic acid to form a gel, and permit the gel to react with MgO for at least about 1 hour. Calcining of the resulting material is critical—it should be calcined preferably at about 300 to about 500 degrees Centigrade for about 1 hour to about 18 hours. Even though the initial treatment of pseudoboehmite with an acid results in a composition which may be called a gel, the reaction of the pseudoboehmite with MgO is a reaction of two solids. The gel may also be referred to as a dispersion of pseudoboehmite crystallites, that is, of small crystals of pseudoboehmite.

A general method for the preparation of the materials includes the following steps described hereafter.

Pseudoboehmite and an acid solution are mixed together, which results in the formation of a sol or gel. The quantities of acid and pseudoboehmite correspond to a atomic ratio of Al/proton between about 0.2 and about 4 but preferably between about 0.8 and about 1.2.

Magnesium oxide is added to the pseudoboehmite slurry in a magnesium to aluminum ratio of about 1:1 to about 10:1, preferably of about 2:1 to about 3:1, and is allowed to react for a period of time between 1 and 24 hours. Heating the reaction mixture is not necessary but will improve the reaction rate. The course of the reaction can be followed by the exothermicity of the reaction and the disappearance of the crystalline magnesium oxide. Moreover, the reactivity index of magnesium oxide (which is related to the crystal size) is not critical; surface areas of MgO lower than 1 $m^2/g$, which corresponds to a very low reactivity and a very slow hydration rate are preferred. The product at this stage of the preparation is a homogeneous thick slurry which is relatively easy to filter. X-ray diffraction patterns recorded on dried samples show the presence of an ill-defined phase which has a layer structure similar to the naturally occurring hydroxy-carbonates described by R. Allman (Am. Min., 53, 1057-59). However, no carbonates are used or found in the synthetic hydroxides made by the above procedure.

Calcining the dried hydroxide in air or inert atmosphere at about 300° to about 500° C. for about 1 to about 24 hours.

As known in the art, many compounds of the elements of the periodic table can be added during any of the steps described above, either as promoters, co-catalysts or catalytic agent. It is also understood that other preparation steps can be added to the above general procedure. For instance, treatment with hydrogen, oxygen or hydrogen sulfide may be used to make a specific catalyst or catalyst support within the scope of this invention.

At any time after filtration, it is also understood that the material can be shaped in various forms by extrusion, spray-drying or compression. Also, the wet product can be deposited as a washed-coat on monoliths or honeycombs of other materials. My catalyst composition is of course effective by itself for various purposes as is described herein and also may be used as a support for other catalytic materials.

FIG. 1 in the drawings is an X-ray diffraction pattern (Cu kα) of magnesium oxide used as reagent in Example 2.

BEST MODE FOR CARRYING OUT THE INVENTION

Following are examples of the preparation and use of the catalyst:

EXAMPLE 1

This example describes a preparation of the catalyst. 81.6 g of glacial acetic acid was added to a slurry containing 89 g of pseudoboehmite ("Versal 850") and 200 ml of deionized water, the mixture being continuously agitated. After 30 minutes approximately, 2 liters of deionized water and 57.6 g of magnesium oxide (Magchem 10-325 from Martin Marietta) were added and the resulting mixture was continuously agitated and heated to 85°-95° C. for 7 hours. This amount of magnesium oxide corresponds to a Mg/Al atomic ratio of 2.6. The white digested solid was then filtered and dried at 110° C. The dried solid was ground and sieved to 30-16 Mesh and calcined at 400° C. for 5 hours in a muffle furnace.

EXAMPLE 2

200 ml of deionized water was introduced with 35 g of pseudoboehmite ("CATAPAL") in a 6 liter glass Erlenmeyer flask. With continuous agitation, 50 g of concentrated nitric acid (70 wt % $HNO_3$) was slowly added to the alumina slurry, causing the formation of a thick colloidal gel. These quantities of acid and pseudoboehmite correspond to a milliequivalent ratio of Al-/anion of about 3.

After 30 minutes, 2 liters of deionized water and 57.6 g of magnesium oxide were added and the resulting mixture was continuously agitated and heated to 85°-95° C. for 7 hours. This amount of magnesium oxide corresponds to a Mg/Al mole ratio of 2.6. The white digested solid was then filtered and dried at 110° C. The dried solid was ground and sieved to 30-16 Mesh and calcined at 450° C. for 60 minutes.

Figure 1:
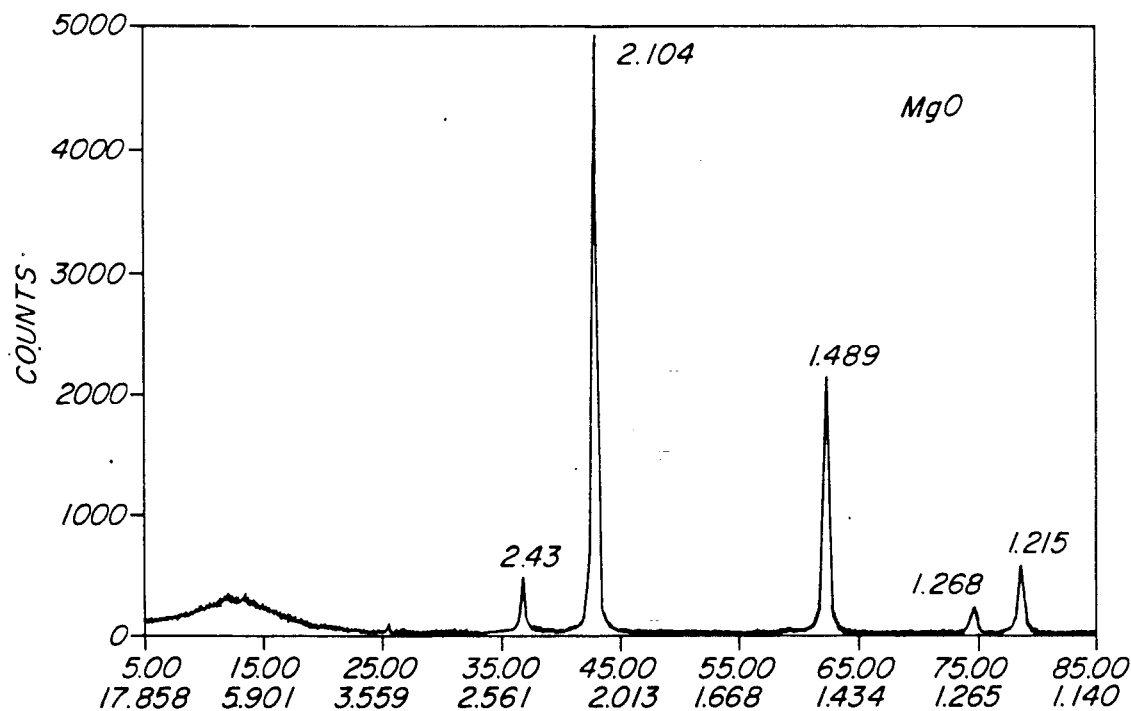
Figure 2:
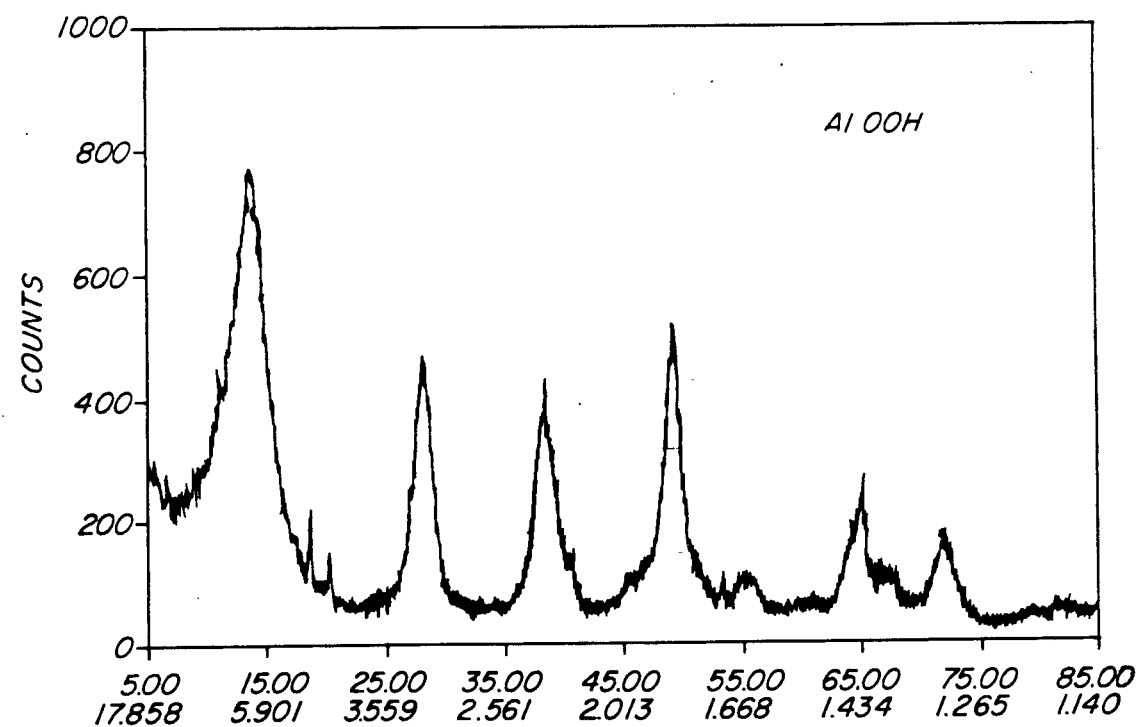
FIG. 2 is an X-ray diffraction pattern (Cu kα) of the pseudoboehmite used as the reagent in Example 2.
Figure 3:
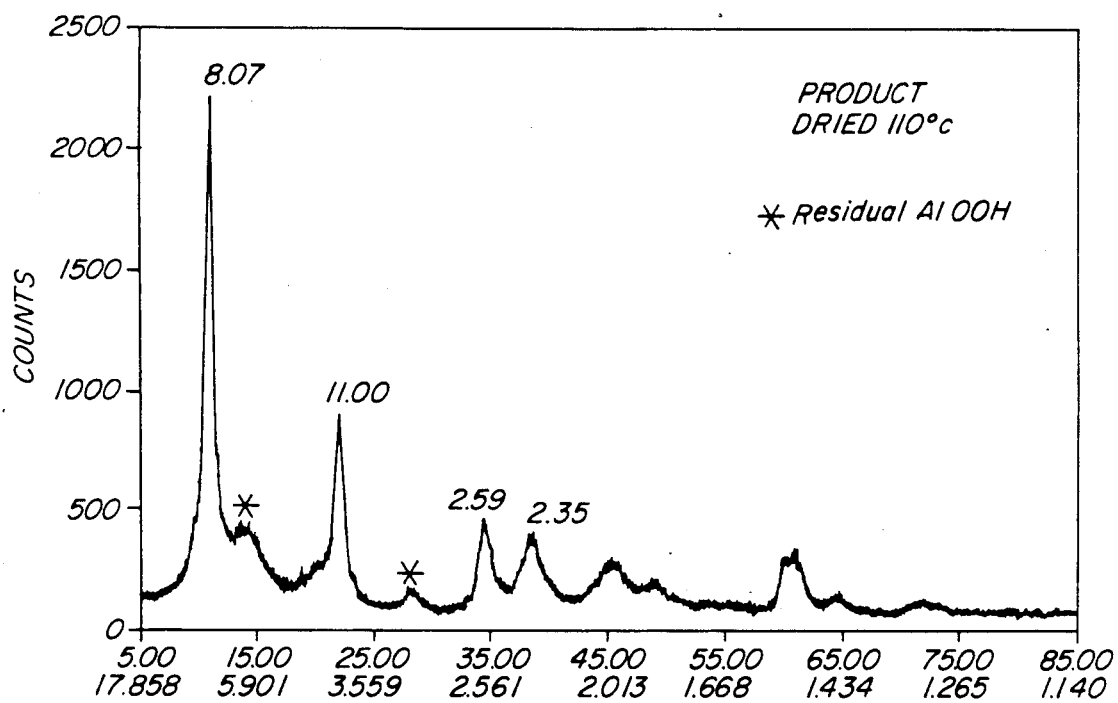
FIG. 3 is an X-ray diffraction pattern (Cu kα) of the dried intermediate product of Example 2, before calcination.
Figure 4:
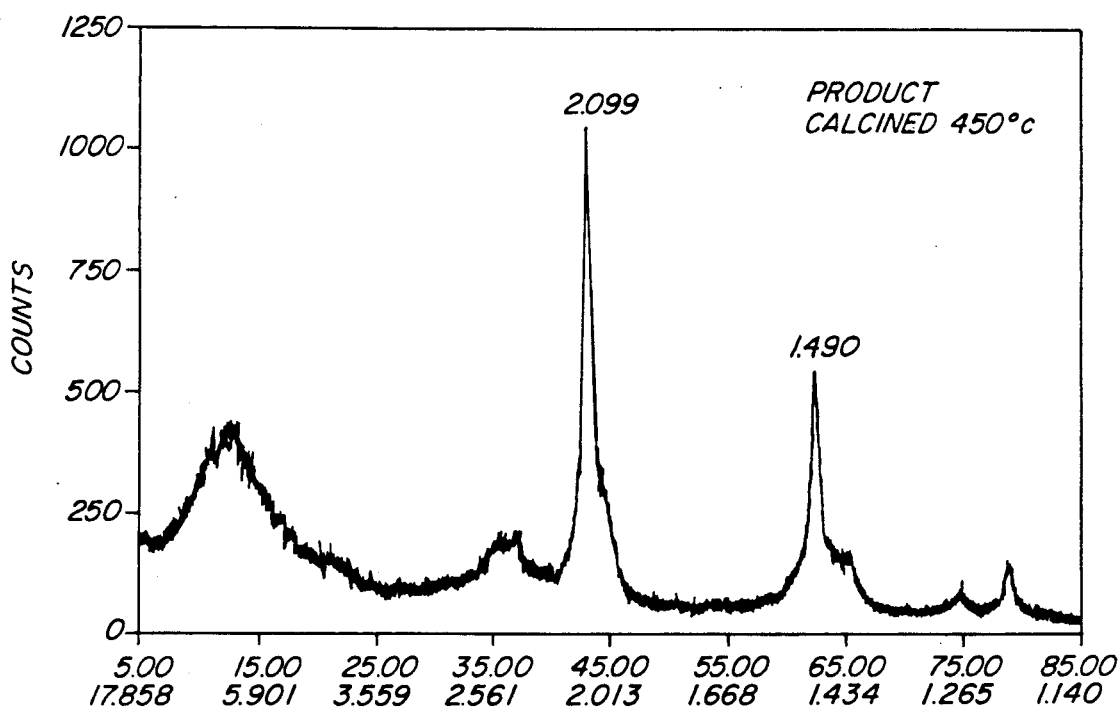
FIG. 4 represents an X-ray diffraction pattern (Cu kα) of the same product calcined at 450° C. for one hour. In each figure, the X-axis represents 2θ and A.

FIG. 1 shows the X-ray pattern (Cu kα radiation) of the MgO; FIG. 2 shows that of the AlOOH, and FIGS. 3 and 4 show those of the resulting formed material before and after calcination. The dried product was identified as a mixed metal hydroxide having a layered brucite-like structure similar to the mineral Hydrotalcite (Joint Committee on Powder Diffraction Standards files #14-191 and 22-700). However, the nitrate anions substitute carbonate anions of the mineral which results in different basal spacings (d003-8.07 instead of d003-7.84). Also, some unreacted pseudoboehmite was detected in the X-ray pattern.

After calcination, the hydrotalcite phase was totally decomposed and a typical X-ray pattern showed the presence of a solid solution of Magnesium-aluminum oxide similar to the structure of periclase (MgO).

A typical X-ray pattern of the catalyst is defined by the presence of two major diffraction peaks having a d-spacing of about 2.099±0.2 Å and 1.490±0.2 Å as shown in FIG. 4.

EXAMPLE 3

81.6 g of glacial acetic acid was added to a slurry containing 89 g of pseudoboehmite (VERSAL 850) and 200 ml of deionzied water. The gel was well homogenized and 3 liters of water added while the mixture was continuously agitated and heated to 70°-80° C. for one hour. 5 liters of water were then added together with 105 g of magnesium oxide. The mixture was stirred and heated at 80°-90° C. for 18 hours. The pH of the cooled suspension was 8.3. The resulting gel was then dried at 110° C. and calcined at 350° C. for 5 hours.

EXAMPLE 4

In order to demonstrate that the catalyst can be used for base catalyzed reactions, a calcined sample of Example 1 has been used to isomerize 1-butene to cis and trans-2-butene. 1 g of material of Example 1 was introduced into a ⅜" tube and a mixture of nitrogen and 1-butene in a volume ratio of about 1:1 was passed through at a flow rate of 30 ml/min. and a temperature of about 150° C. The outlet gas was analyzed by gas chromatography and was found to contain 85.5 % 1-butene, 2.8 % trans-2 butene and 11.6 % cis-2 butene. The ratio cis/trans of 4.1 is consistent with a base catalyzed mechanism.

EXAMPLE 5-7

In order to demonstrate that the catalyst is an effective catalyst for the aldol condensation of ketones, a sample of the catalyst prepared by example 2 was used to condense acetone to mesityl oxide and isophorone. The reaction was carried out in a ⅜" tubular reactor of 316 stainless steel and loaded with 35 g of extruded catalyst. The height of the bed was 8.5 inches. The tests were conducted at 300°, 325° and 350° C. and the feed rate of acetone was adjusted to 40, 104 and 160 ml/hour respectively in order to obtain 30% conversion. The conditions and results of the tests are shown in the table below. Selectivities of mesityl oxide and isophorone were as high as 87% which shows that the catalyst can be used with high efficiency for the aldol condensation of acetone.

|  | Ex: 5 | Ex: 6 | Ex: 7 |
|---|---|---|---|
| Reaction conditions: | | | |
| reaction temperature | 300° C. | 325° C. | 350° C. |
| acetone feed rate (ml/hour) | 40 | 104 | 160 |
| nitrogen flow (ml/min.) | 40 | 23 | 23 |
| pressure (PSIG) | 15 | 15 | 15 |
| Wt % of reactor effluents: | | | |
| acetone | 70.4 | 69.6 | 67.2 |
| mesityl oxide | 3.7 | 3.1 | 3.2 |
| isophorone | 17.8 | 18.9 | 20.4 |
| high boiling products | 4.9 | 5.1 | 5.5 |
| Conversion (wt %) | 29.6 | 30.4 | 32.8 |
| Selectivities (wt %) (dry basis) | | | |
| mesityl oxide | 14.8 | 12.3 | 11.8 |
| isophorone | 72.6 | 74.7 | 74.5 |
| others | 12.6 | 13.0 | 13.7 |
| Total selectivity mesityl oxide + isophorone | 87.4 | 87.0 | 86.3 |

Temperature may be adjusted between about 200° C. and 400° C. or higher, preferably 275° C. to 350° C., with various residence times and/or feed ratio as is known in the art.

EXAMPLE 8-9

The stability of the catalyst was tested for the aldol condensation of acetone with catalysts of example 2 (using nitric acid) and example 1 (using acetic acid). The conditions and results of the experiments are shown in the table below.

|  | Example 8 - Catalyst of Example 2 | Example 9 - Catalyst of Example 1 |
|---|---|---|
| Reaction conditions | | |
| catalyst bed dimensions | ¾ × 28 in. | ½ × 25 in. |
| catalyst charge | 104 g | 40 g |
| pressure | 15 PSIG | 15 PSIG |
| acetone feed rate | 130 ml/hour | 130 ml/hour |
| temperature profile | 305-335° C. | 273-304° C. |
| Results obtained after 500 hours of reaction: | | |
| conversion (wt %) | 42.9 | 24.6 |
| selectivities (wt %) | | |
| mesityl oxide | 7.6 | 15.5 |
| isophorone | 71.5 | 72.9 |
| others | 20.9 | 11.6 |
| Results obtained after 1000 hours of reaction: | | |
| conversion (wt %) | 38.8 | 22.5 |
| selectivities (wt %) | | |
| mesityl oxide | 10.0 | 18.1 |
| isophorone | 72.7 | 73.0 |
| others | 14.3 | 8.9 |

EXAMPLE 10

Aldol condensation of aldehydes has also been tested by condensing n-butyraldehyde to 2-ethyl-hexene-al. 1 g of catalyst of example 3 was introduced into a microreactor and the reaction was conducted at 150° C. Nitrogen was saturated at 35° C. with n-butyraldehyde in a saturator and passed through the catalyst bed at a rate of 24 ml/min. The effluent of the reactor was analyzed by gas chromatrography and was composed of 77 wt % unreacted n-butyraldehyde, 22 wt % of 2-ethyl-hexene-al and 1% of unknown products. The selectivity of condensing the aldehyde to its dimer was 99%. This experiment shows that the catalyst is an effective catalyst for condensing aldehydes selectively.

I claim:

1. The aldol condensation of a ketone conducted at temperature between about 200° C. and about 400° C. in the presence of a catalyst made by a method comprising mixing a water-soluble acid with pseudoboehmite to form a dispersion of pseudoboehmite crystallites, adding MgO or Mg(OH)$_2$ in a ratio of Mg to aluminum in the gel of about 1:1 to about 10:1, agitating the mixture until the MgO or Mg(OH)$_2$ has substantially disappeared, drying the mixture, and calcining it at about 300° to about 500° C. for about 1 to about 24 hours.

2. Aldol condensation of claim 1 wherein the water-soluble acid is acetic acid.

3. Aldol condensation of claim 1 wherein the water-soluble acid is nitric acid.

4. Aldol condensation of claim 1 wherein the atomic ratio of magnesium to aluminum is between about 2:1 to about 3:1.

5. Method of making isophorone and mesityl oxide comprising condensing acetone at about 200° C. to about 400° C. in the presence of a catalyst made by mixing a water-soluble acid with pseudoboehmite to form a dispersion of pseudoboehmite crystallites, adding MgO or Mg(OH)$_2$ in a ratio of Mg to aluminum in the gel of about 1:1 to about 10:1, agitating the mixture until the MgO or Mg(OH)$_2$ has substantially disappeared, drying the mixture, and calcining it at about 300° to about 500° C. for about 1 to about 24 hours.

6. Method of claim 5 wherein the water-soluble acid is acetic acid.

7. Method of claim 5 wherein the water-soluble acid is nitric acid.

8. Method of claim 5 wherein the ratio of magnesium to aluminum is between about 2:1 to abut 3:1.

9. Method of making 2-ethyl-hexene-al comprising condensing n-butyraldehyde in the presence of a catalyst made by mixing a water-soluble acid with pseudoboehmite to form a dispersion of pseudoboehmite crystallites, adding MgO or Mg(OH)$_2$ in a ratio of Mg to aluminum in the gel of about 1:1 to about 10:1, agitating the mixture until the MgO or Mg(OH)$_2$ has substantially disappeared, drying the mixture, and calcining it at about 300° to about 500° C. for about 1 to about 24 hours.

10. The aldol condensation of an aldehyde conducted in the presence of a catalyst made by mixing a water-soluble acid with pseudoboehmite to form a dispersion of pseudoboehmite crystallites, adding MgO or Mg(OH)$_2$ in a ratio of Mg to aluminum in the gel of about 1:1 to about 10:1, agitating the mixture until the MgO or Mg(OH)$_2$ has substantially disappeared, drying the mixture, and calcining it at about 300° to about 500° C. for about 1 to about 24 hours.

* * * * *

UNITED STATES PATENT AND TRADEMARK OFFICE
CERTIFICATE OF CORRECTION

PATENT NO. : 5,055,620

DATED : October 8, 1991

INVENTOR(S) : Alain A. Schutz

It is certified that error appears in the above-identified patent and that said Letters Patent is hereby corrected as shown below:

Column 4, line 49, change "1/8" " to -- 3/8" --.

Signed and Sealed this

Ninth Day of February, 1993

Attest:

STEPHEN G. KUNIN

Attesting Officer   Acting Commissioner of Patents and Trademarks